(12) United States Patent
Slutsky et al.

(10) Patent No.: US 6,462,090 B1
(45) Date of Patent: Oct. 8, 2002

(54) FORMULATIONS FOR DETECTING ASTHMA

(75) Inventors: Arthur Slutsky; Noe Zamel, both of Toronto; Harold Wulffhart, Concord, all of (CA)

(73) Assignee: Ontario Inc., Concord (CA)

( * ) Notice: Subject to any disclaimer, the term of this patent is extended or adjusted under 35 U.S.C. 154(b) by 0 days.

(21) Appl. No.: 09/553,759

(22) Filed: Apr. 21, 2000

Related U.S. Application Data

(60) Provisional application No. 60/130,271, filed on Apr. 21, 1999.

(51) Int. Cl.$^7$ .................... A01N 33/12; A61K 49/00; A61L 9/04
(52) U.S. Cl. ............... 514/642; 424/9.2; 424/45
(58) Field of Search .................. 424/45, 9.2; 514/642

(56) References Cited

U.S. PATENT DOCUMENTS

| | | | |
|---|---|---|---|
| 4,524,769 A | | 6/1985 | Wetterlin ............... 128/203.15 |
| 5,010,056 A | * | 4/1991 | Boghen et al. ............... 514/12 |
| 5,254,330 A | | 10/1993 | Ganderton et al. ........... 424/46 |
| 5,817,028 A | | 10/1998 | Anderson .................... 600/529 |
| 5,985,309 A | * | 11/1999 | Edwards et al. ............ 424/426 |

OTHER PUBLICATIONS

Bell et al., J. Pharmaceut. Sci. 60:1559, 1971.
Newman et al., Eur. Res. J. 2:247, 1989.
American Thoracic Society, "Guidelines for Methacholine and Exercise Challenge Testing—1999", Am J Respir Crit Care Med, 2000, vol. 161, pp. 309–329.*
Underwood et al, "A Novel Technique for the Administration of Bronchodilator Drugs Formulated as Dry Powders to the Anaesthetized Guinea Pig," Journal of Pharmacological Methods, Elsevier Science Publishing, 1991, vol. 26, pp. 203–210.*

* cited by examiner

Primary Examiner—Michael G. Hartley
Assistant Examiner—Michael A. Willis
(74) Attorney, Agent, or Firm—Bereskin & Parr; Anita Nador

(57) ABSTRACT

Improved formulations for detecting asthma are disclosed. The formulations comprise methacholine or histamine in a dry particulate form wherein the particles are of a respirable size, preferably 2 $\mu$m to 5 $\mu$m. The dry formulations can be inhaled directly from an inhaler and can be used to detect airway narrowing which is diagnostic of asthma.

28 Claims, No Drawings

FORMULATIONS FOR DETECTING ASTHMA

This application claims benefit from United States provisional application Ser. No. 60/130,271 filed on Apr. 21, 1999 which is incorporated herein by reference in its entirety.

FIELD OF THE INVENTION

The present invention relates to improved formulations for use in detecting asthma, a method of preparing the new formulations and a method of detecting asthma using the formulations. Preferably the formulations contain methacholine or histamine as the active ingredient.

BACKGROUND OF THE INVENTION

Asthma is a common respiratory disease affecting 5–10% of the population. It is characterized by shortness of breath, cough, airway inflammation and hyper-responsiveness to many stimuli. The diagnosis of asthma is based on the clinical history, physical examination and a number of laboratory tests. A key lab test to diagnose non-specific bronchial hyper-responsiveness is the methacholine challenge.

The methacholine challenge (MC) is the principal test that is used to measure bronchial hyper-responsiveness and hence is a key laboratory test used in the diagnosis of asthma. Methacholine is a bronchoconstrictor which causes a greater degree of airway narrowing in patients with asthma compared to non-asthmatics. The patient's pulmonary function (e.g. FEV1) is measured after each dose until the drop in pulmonary function exceeds a certain degree (e.g. 20% drop in FEV1), or a maximal dose of MC has been given. However, the widespread use of the MC is limited for a number of reasons including:

1. MC is technically difficult to perform: (a) The test is performed by having the subject inhale up to about 10 different concentrations of methacholine (usually doubling doses) via a nebulizer. The methacholine is in solution and a technician has to prepare the different concentrations. This is time consuming, is prone to error and is thus costly. (b) The equipment required is relatively cumbersome, for example, the nebulizer requires a compressor or a compressed gas tank. Furthermore, this equipment is not disposable and thus it has to be cleaned and sterilized after each use. In addition, the output of the nebulizer has to be checked on a regular basis. (c) To deliver the correct amount of methacholine that is inhaled requires some device attached to the nebulizer (e.g. a dosimeter). All of these issues makes the performance of a MC relatively difficult, such that the test is usually performed in a fully equipped laboratory and not in a physician's office. In addition, because of the equipment required, it is not suitable for mass screening of patients.

2. Quality control: Because of the need to prepare various solutions of methacholine, there is the possibility of errors in preparation of the solutions, and errors in the order of administration of the correct doses.

3. Safety: Because of the possibility of errors in preparation of the solutions, a patient may receive too high a dose and this may lead to severe bronchoconstriction.

In view of the foregoing, there is a need in the art for a method for detecting asthma which overcomes the difficulties described above.

SUMMARY OF THE INVENTION

The present invention provides improved formulations for use in detecting asthma. The novel formulations provide methacholine or histamine in ready to use powder formulations which can be inhaled directly through an inhaler in order to test for air narrowing which is diagnostic of asthma. The test can be performed at varying concentrations by varying the dose released from the inhaler. This overcomes the drawbacks of the methacholine challenge test of the prior art where several different solutions of methacholine at varying concentrations must be prepared. The prior art method is thus time consuming, prone to error and costly. In contrast, the method of the present invention can be self-administered or administered with very little supervision.

In one aspect, the present invention provides a formulation for use in detecting asthma comprising methacholine or histamine in a dry particulate form. The formulation is a composite material comprising discrete particles which are a mixture of methacholine or histamine and a carrier. In the preferred embodiment of the invention, the particles of the formulation are methacholine or histamine/sugar composite particles (where sugar is the carrier). In a preferred embodiment, the methacholine or histamine is combined with a pharmaceutically acceptable sugar, preferably of a pharmaceutical grade. Preferably the sugar is a regular grade and pharmaceutical grade sugar.

The methacholine or histamine are combined with the carrier in such a way that it will be delivered to the alveoli and lower airways of a person with the carrier. The composite particles of the formulation are formed in such a way that they have a median particle size to enable the methacholine to be conveyed on inhalation to the alveoli and lower airways of a person. Preferably the size of the particles in the formulation are from 0.1 $\mu$m to 10 $\mu$m, more preferably from 2 $\mu$m to 8 $\mu$m and most preferably from 2 $\mu$m to 5 $\mu$m.

In another aspect, the present invention provides a method of preparing a methacholine or histamine formulation for use in detecting asthma comprising:

(a) combining methacholine or histamine, a pharmaceutical grade sugar and a liquid carrier to produce a flowable mixture; and, (b) drying the flowable mixture at conditions to produce a composite material containing methacholine or histamine/sugar composite particles suitable for delivery to the alveoli and lower airways of a person.

In one embodiment the liquid carrier is water.

The flowable mixture is preferably dried by spray drying. In one embodiment the flowable mixture is atomized prior to being dried. The conditions under which the flowable mixture is spray dried is controlled to produce the desired particle size. In one embodiment the flowable mixture is preferably dried at conditions to form substantially spherical particles. More preferably, the flowable mixture is dried at conditions to from spherical particles which have a dimpled surface.

In a further aspect, the present invention provides a method for detecting asthma in a person comprising (a) having the person inhale an effective amount of a methacholine or histamine formulation in dry particulate form of the invention containing particles of respirable size and (b) measuring airway narrowing, wherein a narrowing of the airways is diagnostic of asthma.

An advantage of the instant invention is that the particles produced by the method disclosed herein are well adapted for delivery to the alveoli and small airways of the lungs with minimal or no impact upon the throat or upper airways of the person, thus preferably resulting in no irritation.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Methacholine Formulation

As hereinbefore mentioned, the present invention provides a methacholine formulation comprising methacholine in a dry particulate form for use in detecting asthma. The methacholine formulation is a composite material comprising discrete particles which are a mixture of methacholine or histamine and a carrier in a form suitable for inhalation by a user. In the preferred embodiment of the invention, the particles of the formulation are methacholine or histamine/sugar composite particles (where sugar is the carrier). Preferably, the sugar is lactose. In particular, the formulation comprises solid discreet flowable particles which may be entrained in the air inhaled by a person so as to travel to the alveoli and smaller airways of the lungs.

The particle size of the methacholine formulation is of a "respirable particle size" which is a size sufficient to enable the methacholine to be conveyed on inhalation to the alveoli and lower airways of a person. Preferably the particle will not settle out, impact or otherwise irritate the patient's throat. Preferably the size of the particles in the formulation are from 0.1 $\mu$m to 10 $\mu$m, more preferably from 2 $\mu$m to 8 $\mu$m and most preferably from 2 $\mu$m to 5 $\mu$m, based on mass median aerodynamic diameter (MMADD)

In a preferred embodiment the methacholine is combined with a pharmaceutically acceptable sugar. A person skilled in the art would understand that the sugar selected should be safe for inhalation. The sugar is preferably selected from lactose, dextrose, glucose, maltose, trehalose or combinations thereof and is most preferably lactose. The sugar may be a natural or a synthetic sugar and may include analogs or derivatives of sugars. The sugar acts as a carrier and, therefore, any form of sugar approved as an excipient may be used. The sugar is preferably of a pharmaceutical grade such as CP, USP, NF, BP, EP or BPC. The sugar should also be of a grade which results in the formation of the desired formulation. Preferably, the sugar should not be pre-treated or spray dried. Preferably, the sugar should be a "regular grade" sugar, such as preferably of a grade like $310 Regular NF Lactose Monohydrate from Formost. The sugar which is used as a starting material is therefore in the form of a dry powder which is readily soluble in water.

The methacholine formulation of the present invention may be prepared by a method comprising:

(a) combining methacholine, a pharmaceutical grade sugar and a liquid carrier to produce a flowable mixture; and, (b) drying the flowable mixture at conditions to produce a composite material containing methacholine/sugar composite particles suitable for delivery to the alveoli and lower airways of a person.

Themethacholine may be any form of methacholine which is soluble in or miscible with the liquid carrier. For example, the methacholine may be a methacholine base. Alternately, or in addition, the methacholine may be a salt. The methachoine may be pharmacologically active analogs or derivatives of methacholine or substances which mimic the effect of methacholine, either alone or in combination with other active substances.

The liquid carrier is an agent which mixes with the sugar and the methachoine to a degree sufficient to form a flowable mixture. The liquid carrier may be any liquid or liquids with which the methacholine may be mixed and the sugar may be dissolved to form a flowable mixture which is preferably of a generally uniform composition. Methacholine bases are generally miscible in water and methacholine salt formulations are generally soluble in water. Further, sugars such as lactose are soluble in water. Accordingly, whether the methacholine is a base and/or a salt formulation, the liquid carrier may comprise water. When a salt is used, the liquid carrier solubilizes the methacholine and the sugar. When a methacholine base is used, the liquid carrier solubilizes the sugar and mixes with the liquid base to create a generally uniform solution (eg. it is miscible with the liquid base). While water is the preferred liquid carrier, other liquids in combination with or in place of water may be used. For example, alternate liquids may be used, either by themselves or in combination to water, to solubilize the solid material or to disperse the methacholine base in the liquid carrier. For example, alternate liquids may be used, either by themselves or in combination to water, to solubilize the solid material or to disperse the nicotine base in the liquid carrier.

In a further preferred embodiment, the liquid carrier may comprise a mixture of alcohol and water. The water and the alcohol form an azeotropic mixture. Methacholine base formulations are readily soluble in an alcohol. However, the lactose is not soluble in the alcohol. Pursuant to this embodiment, the flowable mixture may comprise less water thus assisting in the rate of drying of the flowable mixture and/or the amount of water in the dried product.

Preferably, the alcohol is a primary alcohol. Further, the alcohol is preferably a lower alkyl alcohol (i.e. $C_1$ to $C_5$). A particularly preferred alcohol which may used as a solvent for the methacholine base solution is ethanol. The ethanol may be CP grade, and preferably, is, USP grade. However, it will be appreciated that it is preferable, where possible, to avoid the use of alcohol in the base solution.

This liquid carrier preferably contains an excess amount of water compared to alcohol where alcohol is necessary as a cosolvent. In such an embodiment, the mixture preferably comprises a minor proportion of alcohol and a major proportion of water. Where alcohol is required, the ratio of alcohol to water in the liquid carrier may be from about 1:1 to 1:10, preferably from about 1:2 to 1:8 and more preferably from about The liquid carrier (eg. water) may be mixed with the methacholine to produce a liquid mixture to which the sugar may then be added. Accordingly, the sugar and a methacholine salt may be dissolved in water (or other suitable liquid carrier) to form the flowable mixture. Alternately, the sugar may be dissolved in water and the methacholine base may be mixed with the water to form the flowable mixture. It will be appreciated that the methacholine, liquid carrier and sugar may be combined together in any desired order to produce the dry flowable mixture.

According to the preferred embodiment of this invention, the methacholine compound is added to the water and mixed until a relatively consistent solution is achieved. Sugar is dissolved in water. Subsequently, the mixture of the methacholine in water is added to the aqueous sugar solution and mixed until the flowable product is produced. The mixing may be conducted by any means known in the art.

The amount of liquid mixture which is utilized is sufficient to produce a flowable mixture. Pursuant to the preferred embodiment, the mixture is finely divided (such as passing the flowable mixture through an orifice) on entry to a spray dryer, such as a Buchi-B191 Spray Dryer. The orifice is of a size which enables formation of particle sizes within the preferred ranges of the invention. The desired orifice size would be readily apparent to a person skilled in the art. Accordingly, the flowable mixture is preferably in the form of a liquid or the like, which may readily be finely divided. In one embodiment the flowable mixture can be finely divided by passing the liquid through an atomizer (preferably a rotary atomizer) prior to drying.

The ratio of methacholine to sugar which is dissolved in the flowable mixture will vary upon the concentration of methacholine in the spray dried product. Due to product handling limitations, it is typical in the field that the carrier comprises a substantial portion of the weight of a powder formulation as compared to the active ingredient. The amount of sugar which is utilized, compared to the amount of methacholine, must be sufficient such that the spray dried product can be used in association with dry powder inhalers which are known in the art. Accordingly, the ratio of methacholine to sugar in the flowable mixture may vary and is preferably from about 0.001:10 to about 10:0.001, more preferably from about 0.005:10 to about 1.5:10 and, most preferably, about 0.05:10 to about 1:10 parts by weight. Further, the concentration of methacholine in the flowable mixture may vary and is preferably from about 0.005 to about 1, more preferably from about 0.01 to about 0.6 and most preferably from about 0.01 to about 0.3 w/v (i.e. g/100 ml).

The flowable mixture is dried so as to produce particles which are sized so as to be able to travel to the alveoli and smaller airways of the lungs. Preferably, the particles have a particle size from about 0.1 $\mu$m to about 10 $\mu$m, more preferably from about 2 to about 8 $\mu$m and, most preferably from about 2.0 $\mu$m to about 5 $\mu$m based on the mass median aerodynamic diameter (MMAD) of the particles. The flowable mixture is preferably rapidly dried such as by using a spray drier. However, other drying techniques capable of producing appropriately sized particles (eg. the use of fluidized bed drying) may be used.

The flowable liquid is preferably rapidly dried so as to produce spherical or substantially spherical particles. Such particles may be achieved by using a rotary atomizer to feed the flowable liquid into a spray dryer or by passing the flowable liquid through a suitable sized orifice of a spray dryer which does not have a rotary atomizer, such as a Buchi-B 191 Spray Dryer.

The operating conditions of the spray dryer are adjusted so as to produce particles which are sized so as to be able to travel to the alveoli and smaller airways of the lungs. If a rotary atomizer is used, the rotary atomizer may be operated at a liquid feed rate from about 2 to about 20, more preferably from 2 to about 10, and most preferably from about 2 to about 5 ml/min. The rotary atomizer may be operated from about 10,000 to about 30,000, more preferably from about 15,000 to about 25,000, and most preferably from about 20,000 to about 25,000 rpm.

The spray dryer is operated at temperatures sufficiently high to cause the liquid carrier to rapidly evolve without raising the temperature of the sugar and methacholine to a point at which these compounds commence to degrade. Accordingly, the spray dryer is preferably be operated with an inlet temperature from about 120 to about 210° C., preferably from about 120 to about 170° C. and more preferably at about 160° C., and an outlet temperature from preferably about 50 to about 130° C., or more preferably from about 50 to about 100° C., or more preferably from about 70 to about 100° C., and most preferably at about 81° C.

The medicament particles are spherical or of another aerodynamic shape. Such particles will tend not to aggregate when stored in a bulk form. Further, by evolving the liquid carrier sufficiently rapidly during the spray drying process, the medicament particles may be produced with an uneven or a "dimpled" surface. The uneven surface produces turbulence as the particles travel through the air, thus providing the particles with aerodynamic lift. This assists the particles to be entrained, and to remain entrained, in the air inhaled by a user thus improving the ability of the medicament particles to travel to the alveoli and smaller airways.

The final product (methacholine-lactose composite) contain various concentrations of methocholine as desired. It is preferably from about 0.1 to about 20%, more preferably from about 0.1 to about 10.5% and most preferably between about 0.5 to about about 10.% (wt/wt).

Histamine Formulation

The above described method for preparing the methacholine formulations can be employed to prepare dry particulate formulations of histamine.

Method for Detecting Asthma

The novel methacholine and histamine formulations of the present invention can be used in the detection of asthma. Accordingly, the present invention provides a method for detecting asthma in a person comprising (a) having the person inhale into his/her airways an effective amount of a methacholine or histamine formulation in dry particulate form containing particles of respirable size and (b) measuring airway narrowing, wherein a narrowing of the airways is diagnostic of asthma.

"Particulates of a respirable size" means particles that are able to be drawn into the airways of the person's lungs and will not settle out against the person's mouth or throat. Preferably the particles are form 0.1 $\mu$m to 10 $\mu$m, more preferably from 2 $\mu$m to 8 $\mu$m and most preferably from 2 $\mu$m to 5 $\mu$m, based on MMAD. The methacholine or histamine formulation preferably contains a pharmaceutical grade sugar, more preferably lactose.

The methacholine or histamine formulation can be administered through a conventional dry powder inhaler which are compact, portable and easy to use. Breath activated inhalers having a housing, an air conduit adapted to conduct air flow to a patient, and means for introducing a medicament into the air conduit are generally known in the art, see, for example, U.S. Pat. No. 4,524,769 to Wetterlin; Bell et al., J. Pharmaceut. Sci. 60:1559, 1971 and Newman et al., Eur. Res. J. 2:247, 1989. Examples of suitable inhalers include SPINHALER®, TURBHALER®, ROTAHALER®, CYCLOHALER®, INHALATOR® and DISKHALER®. Breath activated inhalers differ from pressurized aerosol inhalers in that breath activated inhalers are activated by inhalation of the user so that the medicament is reliably drawn into the distal regions of the lung.

In order to perform the method of the present invention, the person being tested inhales the methacholine or histamine formulation from a breath activated inhaler. Preferably, the person is subjected to a series of tests, each at a higher dose of the methacholine or histamine. After each test the person will be tested for airway narrowing, preferably by measuring the Forced Expiratory Volume in one second (FEV1) using techniques known in the art. If airway narrowing is detected, then the person has asthma. Generally, if there is a 20% or greater reduction in the FEV1 compared with a baseline control then the person has asthma.

The following non-limiting examples are illustrative of the present invention

EXAMPLES

Example 1
Preliminary Tests for the Preparation of the Methacholine Formulation 1) Characterization of Materials Received The material received was characterised using scanning Electron Microscope (SEM), to provide useful information for determining suitable composite formation conditions by spray drying.

2) Feasibility Study for Producing 2–5 μm Particles of Methacholine Lactose Composite Powder a) Drug powder of 5% wt/wt Methacholine in Lactose. Initial experiments indicated that spray drying technology is possible for producing spherical drug particles having a size range between 2 and 5 μm from an aqueous solution. The adjustment of spraying operating conditions results in a strict particle size range. To meet the size requirements, droplets should have a narrow size distribution and a short residence time to avoid coagulation prior to drying. Experiments were conducted using a Laboratory spheroniser equipped with a rotary atomiser. Results are shown in Table 1. Note particle size was estimated from SEM. A more precise analysis would be obtained using thermogravimetric analysis (TGA) or x-ray diffraction (XRD) or laser diffraction.

3) Determination of appropriate spray drying conditions

Suitable spray drying conditions, including drying temperature, spinning speed of the atomiser wheel, solution feedrate and concentration of the solutes were determined experimentally to produce the composite powder according to required specifications. Results are listed in Tables 1 and 2.

Example 2
Preparation of Methchoine Formulations

A number of methacholine formulations were prepared as indicated in Table 3. Methacholine and lactose in amounts listed in Table 3 were added to 485 grams of water. The mixture was stirred until the solution was clear (approximately 5 minutes). The mixture was spray dried in a Buchi Mini Spray Dryer -B 191, with an air flow rate of 600 ml/minute, and inlet and outlet temperature as indicated in Table 3. The methacholine and lactose solution was fed into the dryer at a flow rate setting as indicated in Table 3. The results are set out in Table 3.

Determination of Methacholine content in Methacholine-Lactose composite product was done using Capillary Electrophoresis (wavelength of detection=214 nm), using standard methods known in the art. The acetyl-β-methacholine chloride in lactose methacholine was assayed using the following parameters:

Column: a 97 cm uncoated capillary 50 um I.D. column
Wavelength: 214 nm
Indirect detection
Injection: 5 seconds
Voltage: 30 kV
Buffer: 2 mM Imidazole, pH 3.0

Capillary was rinsed with buffer for 2 minutes prior to injection The buffer was prepared by dissolving 136 mg imidazole in 50 ml of water. The pH was then adjusted to 3.0 with 0.5 N HCL. Volume was then adjusted with water to 100 ml. The buffer was then filtered with a 0.45 μm filter. Acetyl-β-Methacholine Chloride (1 mg/ml) standard was prepared by placing 100 mg of standard in 1000 ml of water.

Particle size was determined using SEM microscopy. It should be noted that sizes listed in Table 3 indicate an estimation of what all particle sizes in the formulation are under. A more precise measurement, using laser diffraction method would indicate that the median aerodynamic diameter (MMAD) of the particles were between about 2 to about 5 microns.

Methacholine formulations were prepared with 0.5, 2.0, 5.0 and 10% wt/wt methacholine in finished product (see example nos. 13–16 in Table 3). All the formulations showed good flowability. Example 12, which had a methacholine content in an amount higher than about 10% (i.e, above about 10.25%) in Methacholine-Lactose composite product, under the conditions used in Table 3 produced wet or very wet compound, which did not have the desired flowability for a dry powder inhaler. Varying the conditions may produce a final dry product with higher Methacholine concentrations.

Although a range of inlet and outlet temperatures of the spray drier could work, the optimal inlet temperature was 160° C., while the optimal outlet temperature of the spray dryer was 81° C., at a solution feed rate of 35%.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Test Matrix for the Determination of Suitable Spray Drying Conditions.

| | Drug Substance | Powder produced | T° drying (Centigrade) | rpm atomiser | feedrate (ml/min) | Solute % wt | Mean Size* (Micron) |
| --- | --- | --- | --- | --- | --- | --- | --- |
| 1 | Methacholine | Imp. 01 | 132 | 25500 | 10 | 14 | 32 |
| 2 | methacholine | Imp. 02 | 126 | 25500 | 10 | 10 | 25 |
| 3 | Methacholine | Imp. 03 | 135 | 25500 | 10 | 5 | 16 |
| 4 | Methacholine | Imp. 04 | 130 | 25500 | 10 | 3 | 6 |

*Estimated from SEM Micrographs

TABLE 2

| Time | Exit Temperature ° C. | Downstream heater temperature ° C. | Exhaust Temperature ° C. | Atomiser Air Pressure Kg/cm² |
|---|---|---|---|---|
| 16.11 | 125 | 97 | 79.9 | 5.5 |
| 16.2 | 129 | 89 | 78.9 | 5.2 |
| 5.61 | 134 | 88 | 74.2 | 5.6 |
| 16.42 | 130 | 86 | 72.1 | 5.2 |
| 17 | 130 | 86 | 71.6 | 5.6 |
| 17.3 | 130 | 86 | 71.7 | 5.6 |
| 17.45 | 130 | 86 | 72.2 | 5.2 |
| 18.05 | 130 | 86 | 72.1 | 5.2 |
| 18.2 | 130 | 86 | 72.1 | 5.2 |
| 18.45 | 130 | 86 | 72.1 | 5.8 |
| 19.05 | 130 | 86 | 72 | 5.2 |

TABLE 3

EXPERIMENTAL PART FOR PREPARATION OF METHACHOLINE-LACTOSE COMPOSITE PRODUCT

| No | Methacholine added (g) | Lactose added (g) | Water added (g) | Methacholine: Lactose ratio | Methacholine concentration in solution % (w/v) | Air Flow ml/min | Solution Feed Rate % | Inlet Temp (° C.) | Outlet Temp (° C.) | Particle Size (μ) | Methacholine concentration in Finished Product % (w/w) | Description of powder |
|---|---|---|---|---|---|---|---|---|---|---|---|---|
| 1 | 0.9125 | 14.1025 | 485 | 0.0647 | 0.1881 | 600 | 35 | 130 | 51 | not done | not done | dry |
| 2 | 0.9125 | 14.1025 | 485 | 0.0647 | 0.1881 | 600 | 35 | 160 | 69 | not done | not done | very wet |
| 3 | 0.9125 | 14.1025 | 485 | 0.0647 | 0.1881 | 600 | 24 | 160 | 86 | not done | not done | dry |
| 4 | 0.9146 | 14.1068 | 485 | 0.0648 | 0.1886 | 600 | 35 | 130 | 57 | <6 | 6.45 | dry |
| 5 | 0.9146 | 14.1068 | 485 | 0.0648 | 0.1886 | 600 | 35 | 160 | 81 | <7 | 6.48 | dry |
| 6 | 0.9146 | 14.1068 | 485 | 0.0648 | 0.1886 | 600 | 35 | 190 | 98 | <8 | 6.56 | dry |
| 7 | 0.9146 | 14.1068 | 485 | 0.0648 | 0.1886 | 600 | 18 | 190 | 116 | <7 | not done | dry |
| 8 | 1.8250 | 14.1025 | 485 | 0.1294 | 0.3763 | 600 | 24 | 160 | 86 | not done | not done | very wet |
| 9 | 1.8250 | 14.1025 | 485 | 0.1294 | 0.3763 | 600 | 24 | 190 | 103 | not done | not done | very wet |
| 10 | 1.8230 | 14.1128 | 485 | 0.1291 | 0.3759 | 600 | 18 | 190 | 119 | not done | not done | wet |
| 11 | 1.8230 | 14.1128 | 485 | 0.1291 | 0.3759 | 600 | 18 | 203 | 127 | not done | not done | very wet |
| 12 | 1.8230 | 14.1128 | 485 | 0.1291 | 0.3759 | 600 | 35 | 160 | 81 | not done | 12.76 | very wet |
| 13 | 0.0700 | 14.0000 | 485 | 0.0050 | 0.0144 | 600 | 35 | 160 | 81 | <8 | 0.57 | dry |
| 14 | 0.2800 | 14.000 | 485 | 0.0200 | 0.0577 | 600 | 35 | 160 | 81 | <6 | 2.23 | dry |
| 15 | 0.7000 | 14.0000 | 485 | 0.0500 | 0.1443 | 600 | 35 | 160 | 81 | <6 | 4.97 | dry |
| 16 | 1.4000 | 14.000 | 485 | 0.1000 | 0.2887 | 600 | 35 | 160 | 81 | <7 | 10.23 | dry |

We claim:

1. A dry powder methacholine formulation for administration to the lungs consisting of composite particles of a respirable particle size and consisting of methacholine and a pharmaceutical grade sugar.

2. The formulation according to claim 1 wherein the sugar is lactose.

3. The formulation according to claim 2 wherein the particles are about 0.1 μm to about 6 μm in size based on mass median aerodynamic diameter.

4. The formulation according to claim 3 wherein the particles are about 2 μm to about 6 μm in size based on mass median aerodynamic diameter.

5. The formulation according to claim 4 wherein the particles are about 2 μm to about 5 μm in size based on mass median aerodynamic diameter.

6. The formulation according to claim 5 wherein the particles are spherical.

7. The formulation according to claim 6 wherein the particles have a dimpled surface.

8. The formulation of claim 5 wherein the amount of methacholine is from about 0.1 to about 10.5% wt/wt.

9. A method of detecting asthma in a person comprising:
(a) having the person inhale into his/her airways an effective amount of a methacholine formulation according to any one claims 1 to 8, and
(b) measuring airway narrowing, wherein a narrowing of the airways is diagnostic of asthma.

10. A method according to claim 9 wherein airway narrowing is measured by measuring the Forced Expiratory Volume in one second (FEV1).

11. A method of preparing a methacholine formulation comprising:
(a) combining methacholine, a pharmaceutical grade sugar and a liquid carrier to produce a flowable mixture; and
(b) drying the flowable mixture to produce a composite material at conditions to produce composite particles consisting of methacholine and the sugar that are of a respirable particle size suitable for delivery to the alveoli and lower airways of a person.

12. The method according to claim 11 wherein the pharmaceutical grade sugar is lactose.

13. The method according to claim 12, wherein the liquid carrier is water.

14. The method according to claim 13, wherein the ratio of lactose to methacholine in the flowable mixture is from about 0.001:10 to about 10:0.0001 parts by weight and the concentration of methacholine varies from about 0.005 to about 1% w/v.

15. The method according to claim 11, wherein the flowable mixture is spray dried.

16. The method according to claim 15, wherein the temperature of the spray drier at the inlet is between about 120 to about 170° C. and the temperature at the outlet is between about 50 to about 100° C.

17. The formulation of claim 3 wherein the amount of methacholine is from about 0.1 to about 10.5% wt/wt.

18. The method of claim 11 wherein the respirable particle size is about 0.1 μm to about 6 μm based on mass median aerodynamic diameter.

19. The method of claim 18 wherein the respirable particle size is about 2 μm to about 6 μm based on mass median aerodynamic diameter.

20. The method of claim 19 wherein the respirable particle size is about 2 μm to about 5 μm based on mass median aerodynamic diameter.

21. The formulation produced by the method of claim 11.

22. The formulation produced by the method of claim 16.

23. A dry powder composite particle consisting of methacholine and a pharmaceutical grade sugar that has a respirable particle size suitable for administration to the lungs.

24. The dry powder composite particle of claim 23 having a respirable particle size of between 0.1 μm to 6 μm based on mass median aerodynamic diameter.

25. The dry powder composite particle of claim 24 having a respirable particle size of between 2 μm to 6 μm based on mass median aerodynamic diameter.

26. The dry powder composite particle of claim 25 having a respirable particle size of between 2 μm to 5 μm based on mass median aerodynamic diameter.

27. A method of detecting asthma in a person comprising:

(a) having the person inhale into his/her airways an effective amount of the composite particle according to claim 23, and (b) measuring airway narrowing, wherein a narrowing of the airways is diagnostic of asthma.

28. A method according to claim 27, wherein airway narrowing is measured by measuring the Forced Expiratory Volume in one second (FEV1).

* * * * *

UNITED STATES PATENT AND TRADEMARK OFFICE
CERTIFICATE OF CORRECTION

PATENT NO. : 6,462,090 B1  Page 1 of 1
DATED : October 8, 2002
INVENTOR(S) : Arthur Slutsky, Noe Zamel and Harold Wulffhart It is certified that error appears in the above-identified patent and that said Letters Patent is hereby corrected as shown below:

<u>Title page,</u>
Item [73], Assignee incorrectly reads: "Ontario Inc., Concord (CA)" and hereby changed to read -- 1355540 Ontario Inc., Concord (CA) --

Signed and Sealed this

Eighteenth Day of March, 2003

JAMES E. ROGAN
*Director of the United States Patent and Trademark Office*